US010059671B2

(12) United States Patent
Potnick

(10) Patent No.: US 10,059,671 B2
(45) Date of Patent: Aug. 28, 2018

(54) POSITIVE ALLOSTERIC MODULATORS OF MGLUR3

(71) Applicant: Merck Patent GmbH, Darmstadt (DE)

(72) Inventor: Justin Potnick, Acton, MA (US)

(73) Assignee: PREXTON THERAPEUTICS SA, Geneva (CH)

( * ) Notice: Subject to any disclaimer, the term of this patent is extended or adjusted under 35 U.S.C. 154(b) by 0 days.

(21) Appl. No.: 14/765,048

(22) PCT Filed: Jan. 22, 2014

(86) PCT No.: PCT/EP2014/000160
§ 371 (c)(1),
(2) Date: Jul. 31, 2015

(87) PCT Pub. No.: WO2014/117919
PCT Pub. Date: Aug. 7, 2014

(65) Prior Publication Data
US 2015/0361046 A1 Dec. 17, 2015

Related U.S. Application Data

(60) Provisional application No. 61/760,386, filed on Feb. 4, 2013.

(51) Int. Cl.
C07D 217/26 (2006.01)
C07D 213/85 (2006.01)
C07D 491/052 (2006.01)
C07D 495/04 (2006.01)
A61K 31/438 (2006.01)
A61K 31/472 (2006.01)
A61K 31/5377 (2006.01)

(52) U.S. Cl.
CPC .......... *C07D 217/26* (2013.01); *A61K 31/438* (2013.01); *A61K 31/472* (2013.01); *A61K 31/5377* (2013.01); *C07D 213/85* (2013.01); *C07D 491/052* (2013.01); *C07D 495/04* (2013.01)

(58) Field of Classification Search
None
See application file for complete search history.

(56) References Cited

U.S. PATENT DOCUMENTS

| 6,498,180 | B1 | 12/2002 | Collado Cano et al. |
| 6,699,873 | B1 | 3/2004 | Maguire et al. |
| 6,833,364 | B1 | 12/2004 | Straub et al. |
| 7,598,384 | B2 | 10/2009 | Jirgensons et al. |
| 7,642,264 | B2 | 1/2010 | Gatti McArthur et al. |
| 8,183,262 | B2 | 5/2012 | Gatti McArthur et al. |
| 2003/0225081 | A1 | 12/2003 | Nagato et al. |
| 2004/0142978 | A1* | 7/2004 | Anderson ............ C07D 213/85 514/344 |
| 2004/0152739 | A1* | 8/2004 | Hanau .................. C07D 401/04 514/341 |
| 2005/0197361 | A1 | 9/2005 | Jirgensons et al. |
| 2006/0189622 | A1 | 8/2006 | Nagato et al. |
| 2007/0232583 | A1 | 10/2007 | McArthur et al. |
| 2009/0318474 | A1 | 12/2009 | Gatti McArthur et al. |

FOREIGN PATENT DOCUMENTS

| DE | 19834047 A1 | 2/2000 |
| EP | 1074549 A2 | 2/2001 |
| EP | 1319659 A1 | 6/2003 |
| WO | 0075101 A1 | 12/2000 |
| WO | 03093236 A1 | 11/2003 |
| WO | 2004054505 A2 | 7/2004 |
| WO | 2005082856 A2 | 9/2005 |
| WO | 2007110337 A1 | 10/2007 |
| WO | 2008112440 A1 | 9/2008 |
| WO | 2009015897 A1 | 2/2009 |
| WO | 2010089119 A1 | 8/2010 |
| WO | 2012085167 A1 | 6/2012 |

OTHER PUBLICATIONS

Murray et al, (Pharmacol Biochem and Behavior 73:455-466, 2002).*
Corti et al (J Neurosci 27:8297-8308, 2007).*
Anderson (Chem and Biol 10:787-797, 2003).*
Thiel (Nature Biotechnol 2:513-519, 2004).*
Sheffler et al (Bioorg Med Chem 22:3921-3925, 2012).*
STN Summary (Accession No. 1991:429161)—containing summary of Paronikyan et al (Armyanskii Khimicheskii Zhurnal 42(12):766-773, 1989).*
International Search Report from PCT Application No. PCT/EP2014/000160 dated Apr. 4, 2014.
Database Registry, Chemical Abstracts Service, XP002721673, (2001).
Database Registry, Chemical Abstracts Service, XP002722034, (2000).
Database Registry, Chemical Abstracts Service, XP002722035, (2001).
Database Registry, Chemical Abstracts Service, XP002722036, (2011).
Database Registry, Chemical Abstracts Service, XP002722037, (2006).
Database Registry, Chemical Abstracts Service, XP002722038, (2001).
Database Registry, Chemical Abstracts Service, XP002722039, (2001).
Database Registry, Chemical Abstracts Service, XP002722040, (2001).
Douglas F. Burdi et al. "Design, Synthesis, and Structure-Activity Relationships of Novel Bicyclic Azole-amines as Negative Allosteric Modulators of Metabotropic Glutamate Receptor 5" J. Med. Chem. (2010), vol. 53, pp. 7107-7118.

(Continued)

Primary Examiner — Craig D Ricci
(74) Attorney, Agent, or Firm — Millen White Zelano & Branigan, PC

(57) ABSTRACT

The present invention relates to novel substituted pyridine derivatives as positive allosteric modulators for modulating metabotropic glutamate receptor subtype 3 (mGluR3) and/or altering glutamate level or glutamatergic signalling.

8 Claims, No Drawings

(56) References Cited

OTHER PUBLICATIONS

Peter Ray, et al. "Fragment-based discovery of 6-substituted isoquinolin-1-amine based ROCK-I inhibitors" Bioorganic & Medicinal Chemistry Letters 21 (2011), pp. 97-101.
Search Report from corresponding EP2951157 dated Apr. 19, 2017 (pp. 1-3).

* cited by examiner

POSITIVE ALLOSTERIC MODULATORS OF MGLUR3

TECHNICAL FIELD

The present invention relates to novel substituted pyridine derivatives as positive allosteric modulators for modulating metabotropic glutamate receptor subtype 3 (mGluR3) and/or altering glutamate level or glutamatergic signalling.

PRIOR ART

Glutamate is the major amino-acid transmitter in the mammalian central nervous system (CNS). Glutamate plays a major role in numerous physiological functions, such as learning and memory but also sensory perception, development of synaptic plasticity, motor control, respiration and regulation of cardiovascular function. Furthermore, glutamate is at the center of several different neurological and psychiatric diseases, where there is an imbalance in glutamatergic neurotransmission.

Glutamate mediates synaptic neurotransmission through the activation of ionotropic glutamate receptor channels (iGluRs), namely the NMDA, AMPA and kainate receptors which are responsible for fast excitatory transmission (Nakanishi et al., (1998) Brain Res. Rev., 26:230-235).

In addition, glutamate activates metabotropic glutamate receptors (mGluRs) which have a more modulatory role that contributes to the fine-tuning of synaptic efficacy. The mGluRs are G protein-coupled receptors (GPCRs) with seven-transmembrane spanning domains and belong to GPCR family 3 along with the calcium-sensing, GABAb and pheromone receptors. The mGluR family is composed of eight members. They are classified into three groups (group I comprising mGluR1 and mGluR5; group II comprising mGluR2 and mGluR3; group III comprising mGluR4, mGluR6, mGluR7 and mGluR8) according to sequence homology, pharmacological profile and nature of intracellular signalling cascades activated (Schoepp et al., (1999) Neuropharmacology, 38: 1431-1476).

Glutamate activates the mGluRs through binding to the large extracellular amino-terminal domain of the receptor, herein called the orthosteric binding site. This activation induces a conformational change of the receptor which results in the activation of the G-protein and intracellular signalling pathways.

The Group II mGlu receptors modulate glutamate transmission by second messenger activation via coupling to Gi/o proteins to negatively regulate the activity of adenylyl cyclase. Excessive accumulation of glutamate in the perisynaptic extracellular region triggers mGlu2 and mGlu3 receptors to inhibit further release of glutamate. Thus, there is significant potential for the development of selective Group II mGlu receptor PAMs and NAMs for the treatment of CNS diseases caused by aberrant glutamatergic signaling.

The common end point of Parkinson's disease (PD) pathology is a progressive degeneration of the dopaminergic neurons located in the pars compacta of the substantia nigra (SNpc) that project and release dopamine into the striatum. PD symptoms usually appear when more than 60% of SNpc neurons have already disappeared. This results in profound movements disturbances including rest tremor, rigidity and stiffness, gait and balance control dysfunctions and dementia that dramatically deteriorate patients and family quality of life.

Current treatments aim at substituting the missing dopamine or mimicking its effects by chronically providing patients with the dopamine precursor L-DOPA, inhibitors of dopamine catabolic enzymes (MAO inhibitors) or direct dopamine receptors agonists. Although these treatments proved relatively efficient in controlling the main symptoms of PD, their chronic administration is associated with serious side effects. For example, the efficacy of L-DOPA following few years of treatment invariably tends to diminish in intensity and stability leading to uneven on/off periods that require an increase in dosing. In addition, chronic administration of high doses of L-DOPA is associated with the occurrence of involuntary movements (dyskinesia) that are usually overcome by combining a reduction in the dose of L-DOPA with other dopaminergic agents. Yet, massive supply of dopamine in the brain has also been associated with psychiatric disturbances including depression, psychotic symptoms, obsessive behaviours sleep disturbances etc. Finally, none of the compounds of the current pharmacopeia for PD have demonstrated neuroprotective activity that would delay disease progression. Therefore, to address these important unmet medical needs, efforts are required to develop new treatments for PD that target the neurochemical systems downstream dopamine itself.

The control of movements by dopamine in healthy subjects follows a complex pattern of neurochemical systems and brain structures interactions (Wichmann and Delong, 2003, Adv Neurol 91:9-18). The basal ganglia that is composed mainly of the substantia nigra (SN), and the striatal and thalamic complex constitutes the cornerstone of these interactions. The internal capsule of the globus pallidus (GPi) and SN pars reticulata (SNpr) fulfil the roles of relays between cortical areas that directly control movements and the basal ganglia itself. GPi and SNpr receive both an inhibitory direct connection (direct pathway) and an excitatory indirect input (indirect pathway) from the basal ganglia. Both pathways are modulated by dopamine with opposite valence so that the direct pathway is stimulated while the indirect pathway is inhibited by dopamine. Consequently in the diseased brain, the lack of dopamine leads to a dysregulation of the output activity of both the direct and indirect pathways. In particular, the indirect pathway gets overactivated, which is reflected by increased GABA release into the globus pallidus external segment (GPe). Consequently, glutamate release is increased in the SN pars compacta (SNpc), GPi and SNpr. These distortions of the balance of neurotransmission in the direct and indirect pathways are believed to result in movement control abnormalities and the precipitation of neurodegeneration of dopaminergic neurons. Fine analysis of these pathways provided insights on the possibility to target neurochemical pathways downstream dopamine to restore its function in the PD brain without interfering directly with it. In particular, metabotropic glutamate receptors (mGluRs) have been shown to modulate neurotransmitter release at the presynaptic level.

Activation of group II metabotropic glutamate (mGlu2/3) receptors reduces excessive glutamate release that is often associated with neurodegenerative and psychiatric disorders. LY379268 {(−)-2-oxa-4-aminobicyclo[3.1.0]hexane-4,6-dicarboxylic acid}, which is a highly potent and systemically available mGlu2/3 receptor agonist was effective in several animal model of stroke, epilepsy, drug abuse, schizophrenia, and pain.

Metabotropic glutamate receptors have been shown to modulate neurotransmitter release at the presynaptic level. Specifically, the subtype 3 of mGluRs (mGluR3) predominantly expressed in the central nervous system (CNS), was demonstrated to dampen glutamate neurotransmission at the STN-SNr (Bradley et al., 2000) and cortico-striatal (Lovinger and McCool, 1995) synapses. Evidence suggests that inhibition was achieved through presynaptic mechanisms providing a functional confirmation of the observed presynaptic receptor localization. Furthermore, behavioural and histological analyses confirmed the beneficial effects of stimulating mGluR3 in both symptomatic and neurodegenerative rat models of PD. For example, the cataleptic behaviour observed following haloperidol administration and reserpine-induced immobility were both reversed by non-selective mGluR2/3 agonists (Dawson et al., 2000; Murray et al., 2002; Bradley et al., 2000). Both models mimic key features of the human disease that are rigidity and akinesia, respectively.

Non-selective mGluR2/3 agonists have shown neuroprotection in rats treated with the neurotoxins MPTP or 6-hydroxydopamine (6-OHDA) which selectively kill dopaminergic neurons (Battaglia et al., 2009; Chan et al., 2010). Studies of mGluR2 and mGluR3 knockout mice demonstrate that mGluR3 mediates these neuroprotective effects, at least in part through induction of neurotrophic factor production (Battaglia et al., 2009; Corti et al., 2007). Interestingly, mGluR3 activation has been shown to increase glial glutamate transporter expression (Aronica et al., 2003), suggesting that they could promote extracellular glutamate uptake and protect neurons from excitotoxicity (Zhou et al., 2006; Yao et al., 2005).

Altogether these results suggest that stimulation of mGluR3 has great potential to alleviate PD symptoms in patient and provide neuroprotection to the remaining neurons.

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for mGluR1, mGluR2, mGluR4, mGluR5, mGluR7 and mGluR8 (Knoflach F. et al. (2001) Proc. Natl. Acad. Sci. USA, 98: 13402-13407; Johnson M. P. et al., (2002) Neuropharmacology, 43:799-808; O'Brien J. A. et al., (2003) Mol. Pharmacol., 64:731-740; Johnson M. P. et al, (2003) J. Med. Chem., 46:3189-3192; Marino M. J. et al., (2003) Proc. Natl. Acad. Sci. USA, 100: 13668-13673; Mitsukawa et al., (2005) Proc. Natl. Acad. Sci. USA, 102(51): 18712-18717; Wilson J. et al., (2005) Neuropharmacology, 49:278; for a review see Mutel V., (2002) Expert Opin. Ther. Patents, 12: 1-8; Kew J. N., (2004) Pharmacol. Ther., 104(3):233-244; Johnson M. P. et al., (2004) Biochem. Soc. Trans., 32:881-887; recently Ritzen A., Mathiesen, J. M. and Thomsen C, (2005) Basic Clin. Pharmacol. Toxicol., 97:202-213).

In particular molecules have been described as mGluR3 positive allosteric modulators [Schann, Stephan; Mayer, Stanislas; Franchet, Christel; Frauli, Melanie; Steinberg, Edith; Thomas, Mireille; Baron, Luc; Neuville, Pascal; Journal of Medicinal Chemistry; vol. 53; nb. 24; (2010); p. 8775-8779].

Further prior art documents are as follows:

Paronikyan E G et al. (Armyanskii Khimicheskii Zhurnal 1989, 42(12): 766-773) is directed to the synthesis and anticonvulsant activity of 3-amino derivatives of pyrano[3,4-c]pyridines.

Paronikyan E G et al. (Armyanskii Khimicheskii Zhurnal 1990, 43(8): 518-523) is directed to the synthesis and biological activity of 3-piperazinylpyrano[3,4-c]pyridines.

Paronikyan E G et al. (Armyanskii Khimicheskii Zhurnal 1991, 44(4): 250-257) is directed to the synthesis, transformations and anticonvulsant activity of 3-oxothiopyrano[3,4-c]pyridine derivatives.

Paronikyan E G et al. (Khimiya Geterotsiklicheskikh Soedinenii 1993, 12: 1683-1687) disclose the synthesis of pyrido[2,3-d]pyrimidines condensed with tetrahydropyran and tetrahydrothiopyran.

WO 2001/010842 describes the preparation of melanocortin-4 receptor binding compounds.

WO 2002/062766 relates to the preparation of aryl-substituted tetrahydropyrimidines and related compounds as melanocortin-4 receptor binding compounds.

WO 2004/054505 is directed to the preparation of aminocyanopyridines, in particular tricyclic derivatives, as inhibitors of mitogen activated protein kinase-activated protein kinase-2 for treating TNFalpha mediated diseases.

WO 2004/055015 discloses the preparation of aminocyanopyridines as inhibitors of mitogen activated protein kinase-activated protein kinase-2 for treating TNFalpha mediated diseases.

WO 2005/121100 deals with the preparation of melanocortin-4 receptor binding compounds.

WO 2009/086303 and US 2009/0163545 are directed to a method of using lifespan-altering compounds for altering the lifespan of eukaryotic organisms and screening for such compounds.

WO 2009/051801 discloses chemical inhibitors of inhibitors of differentiation.

Sirakanyan S N et al. (Hayastani Kimiakan Handes 2009, 62(2-4): 378-385) is directed to the synthesis of new derivatives of piperazine-substituted pyrano[3,4-c]pyridines.

Foloppe N et al. (Bioorganic & Medicinal Chemistry Letters 2009, 19(15): 4183-4190) discloses the discovery and functional evaluation of diverse novel human CB1 receptor ligands.

WO 2010/151799 describes compounds for modulating RNA-binding proteins and uses therefor.

Bruno A et al. (Future Medicinal Chemistry 2011, 3(6): 665-681) relate to molecular dynamics simulations and docketing studies on 3D models of the heterodimeric and homodimeric 5-HT2A receptor subtype.

Ripphausen P et al. (Journal of Chemical Information and Modeling 2011, 51(4): 837-824) deal with rationalizing the role of SAR tolerance for ligand-based virtual screening.

The citation of any reference in this application is not an admission that the reference is relevant prior art to this application.

DESCRIPTION OF THE INVENTION

The present invention has the object to provide novel pyridine derivatives.

The object of the present invention has surprisingly been solved in one aspect by providing compounds of formula (I)

wherein:
- $X_1$, $X_2$ independently from each other denote N or CW;
- V denotes an at least one nitrogen atom comprising moiety selected from the group consisting of:
  - (i) NR4R5;
  - (ii) CN;
- R1 independently denotes H, cycloalkyl, aryl, heteroaryl, heterocyclyl or CN, wherein alkyl, cycloalkyl, aryl, heteroaryl, heterocyclyl can optionally be substituted by one or more identical or different substituents T; or R1 and V together with the carbon atoms to which they are attached to form heterocyclyl or heteroaryl comprising at least one nitrogen atom, which can optionally be substituted by one or more identical or different substituents T;
- R2, R3 independently from each other denote H, CN, C(O)—N=C—(NYY)$_2$, alkyl, cycloalkyl, cycloalkylalkyl, aryl, arylalkyl, heteroaryl, heteroarylalkyl, heterocyclyl, heterocyclylalkyl, C(O)-alkyl, C(O)OH, C(O)O-alkyl, wherein alkyl, cycloalkyl, cycloalkylalkyl, aryl, arylalkyl, heteroaryl, heteroarylalkyl, heterocyclyl and heterocyclylalkyl moieties can optionally be substituted by one or more identical or different substituents T; or R2 and R3 together with the carbon atoms to which they are attached to form cycloalkyl, heterocyclyl, aryl or heteroaryl, which can optionally be substituted by one or more identical or different substituents T; or, if $X_2$ is CW, $X_2$ and R3 together with the carbon atoms to which they are attached to form cycloalkyl, heterocyclyl, aryl or heteroaryl, which can optionally be substituted by one or more identical or different substituents T;
- R4, R5 independently from each other denote H, alkyl, cycloalkyl, cycloalkylalkyl, aryl, arylalkyl, heteroaryl, heteroarylalkyl, heterocyclyl, heterocyclylalkyl, which can optionally be substituted by one or more identical or different substituents T;
  - or R4 and R5 together with the nitrogen atom to which they are attached to form heterocyclyl or heteroaryl, which can optionally be substituted by one or more identical or different substituents T;
- W independently from each other denotes H, CN, NYY, alkyl, cycloalkyl, cycloalkylalkyl, aryl, arylalkyl, heteroaryl, heteroarylalkyl, heterocyclyl, heterocyclylalkyl, C(O)—C(O)O-alkyl, wherein alkyl, cycloalkyl, cycloalkylalkyl, aryl, arylalkyl, heteroaryl, heteroarylalkyl, heterocyclyl and heterocyclylalkyl moieties can optionally be substituted by one or more identical or different substituents T;
- T denotes independently from each other alkyl, cycloalkyl, cycloalkylalkyl, aryl, arylalkyl, heteroaryl, heteroarylalkyl, heterocyclyl, heterocyclylalkyl, halogen, F, Cl, Br, I, OH, CN, NO$_2$, NYY, CF$_3$, OCF$_3$, alkyl-OH, alkyl-NYY, alkyl-CN, alkyl-C(O)-heterocyclyl, O-alkyl, O-cycloalkyl, O-alkyl-cycloalkyl, O-aryl, O-alkyl-aryl, O-heteroaryl, O-alkyl-heteroaryl, O-heterocyclyl, O-alkyl-heterocyclyl, O-alkyl-NYY, C(O)OY, C(O)NY-alkyl-NYY, C(O)NYY, C(O)—C(O)—NYY, C(O)-alkyl-NY-alkyl, C(O)-alkyl-NY-alkyl-O-alkyl, C(O)-alkyl, C(O)-cycloalkyl, C(O)-alkyl-cycloalkyl, C(O)-aryl, C(O)-alkyl-aryl, C(O)-heteroaryl, C(O)-alkyl-heteroaryl, C(O)-heterocyclyl, C(O)-alkyl-heterocyclyl, C(O)NY-alkyl, C(O)NY-cycloalkyl, C(O)NY-alkyl-cycloalkyl, C(O)NY-aryl, C(O)NY-alkyl-aryl, C(O)NY-heteroaryl, C(O)NY-alkyl-heteroaryl, C(O)NY-heterocyclyl, C(O)NY-alkyl-heterocyclyl, S(O)$_2$-alkyl, S(O)$_2$-cycloalkyl, S(O)$_2$-alkyl-cycloalkyl, S(O)$_2$-aryl, S(O)$_2$-alkyl-aryl, S(O)$_2$-heteroaryl, S(O)$_2$-alkyl-heteroaryl, S(O)$_2$-heterocyclyl, S(O)$_2$-alkyl-heterocyclyl, wherein alkyl, cycloalkyl, cycloalkylalkyl, aryl, arylalkyl, heteroaryl, heteroarylalkyl, heterocyclyl and heterocyclylalkyl moieties can optionally be substituted by one or more identical or different substituents Z;
- Y denotes independently from each other H, alkyl, cycloalkyl, cycloalkylalkyl, aryl, arylalkyl, heteroaryl, heteroarylalkyl, heterocyclyl, heterocyclylalkyl, wherein alkyl, cycloalkyl, cycloalkylalkyl, aryl, arylalkyl, heteroaryl, heteroarylalkyl, heterocyclyl and heterocyclylalkyl can optionally be substituted by one or more identical or different substituents Z;
- Z denotes independently from each other alkyl, cycloalkyl, cycloalkylalkyl, aryl, arylalkyl, heteroaryl, heteroarylalkyl, heterocyclyl, heterocyclylalkyl, halogen, F, Cl, Br, I, OH, CN, NO$_2$, NH$_2$, NH-alkyl, N(alkyl)$_2$, NH-alkyl-OH, NH-alkyl-O-alkyl, NH-alkyl-aryl, CF$_3$, OCF$_3$, alkyl-OH, alkyl-NH$_2$, alkyl-NH-alkyl, alkyl-N(alkyl)$_2$, alkyl-CN, alkyl-C(O)-heterocyclyl, O-alkyl, O-cycloalkyl, O-alkyl-cycloalkyl, O-aryl, O-alkyl-aryl, O-heteroaryl, O-alkyl-heteroaryl, O-heterocyclyl, O-alkyl-heterocyclyl, O-alkyl-NH$_2$, C(O)OH, C(O)NH-alkyl-NH$_2$, C(O)NH$_2$, C(O)—C(O)—NH$_2$, C(O)-alkyl-NH-alkyl, C(O)-alkyl-NH-alkyl-O-alkyl, C(O)-alkyl, C(O)-cycloalkyl, C(O)-alkyl-cycloalkyl, C(O)-aryl, C(O)-alkyl-aryl, C(O)-heteroaryl, C(O)-alkyl-heteroaryl, C(O)-heterocyclyl, C(O)-alkyl-heterocyclyl, C(O)-heterocyclylalkyl, C(O)NH-alkyl, C(O)NH-cycloalkyl, C(O)NH-alkyl-cycloalkyl, C(O)NH-aryl, C(O)NH-alkyl-aryl, C(O)NH-heteroaryl, C(O)NH-alkyl-heteroaryl, C(O)NH-herterocyclyl, C(O)NH-alkyl-heterocyclyl, C(O)NH-aryl-halogen, C(O)NH-aryl-O-alkyl, C(O)N(alkyl)-aryl, C(O)N(aryl)$_2$, S(O)$_2$-alkyl, S(O)$_2$-cycloalkyl, S(O)$_2$-alkyl-cycloalkyl, S(O)$_2$-aryl, S(O)$_2$-alkyl-aryl, S(O)$_2$-heteroaryl, S(O)$_2$-alkyl-heteroaryl, S(O)$_2$-heterocyclyl, S(O)$_2$-alkyl-heterocyclyl;

and the physiologically acceptable salts, solvates, tautomers and stereoisomers thereof, including mixtures thereof in all ratios.

In a preferred embodiment, a compound according to formula (I) is provided,
wherein:
- R1 denotes CN;
- and the physiologically acceptable salts, solvates, tautomers and stereoisomers thereof, including mixtures thereof in all ratios.

In a preferred embodiment, a compound according to formula (I) and above embodiments is provided, wherein:
- V denotes NR4R5;
- and the physiologically acceptable salts, solvates, tautomers and stereoisomers thereof, including mixtures thereof in all ratios.

In a preferred embodiment, a compound according to formula (I) and above embodiments is provided, wherein:
- R1 and V together with the carbon atoms to which they are attached to form heterocyclyl or heteroaryl, comprising at least one nitrogen atom, which can optionally be substituted by one or more identical or different substituents T;
- and the physiologically acceptable salts, solvates, tautomers and stereoisomers thereof, including mixtures thereof in all ratios.

In a preferred embodiment, a compound according to formula (I) and above embodiments is provided, wherein:

R1 and V together form pyrazolyl, which can optionally be substituted by one or more identical or different substituents T;

and the physiologically acceptable salts, solvates, tautomers and stereoisomers thereof, including mixtures thereof in all ratios.

In a preferred embodiment, a compound according to formula (I) and above embodiments is provided, wherein:

R1 denotes CN;

V denotes NR4R5;

$X_1$ denotes N;

$X_2$ denotes CW;

W denotes alkyl or aryl, preferably ethyl, propyl, isopropyl or phenyl;

R2, R3 independently from each other denote H or R2 and R3 together with the carbon atoms to which they are attached to form cycloalkyl or heterocyclyl, preferably cyclohexyl, tetrahydropyranyl or tetrahydrothiopyranyl, which can optionally be substituted by one or more identical or different substituents T;

R4, R5 independently from each other denote H, alkyl or heterocyclylalkyl, preferably H, ethyl, propyl or morpholinyl-ethyl, which can optionally be substituted by one or more identical or different substituents T, or R4 and R5 together with the nitrogen atom to which they are attached to form heterocyclyl, preferably morpholinyl, which can optionally be substituted by one or more identical or different substituents T;

and the physiologically acceptable salts, solvates, tautomers and stereoisomers thereof, including mixtures thereof in all ratios.

In another aspect, the object of the present invention has surprisingly been solved by providing compounds selected from the group consisting of:

| Compound No. | Chemical Structure |
|---|---|
| 1 | 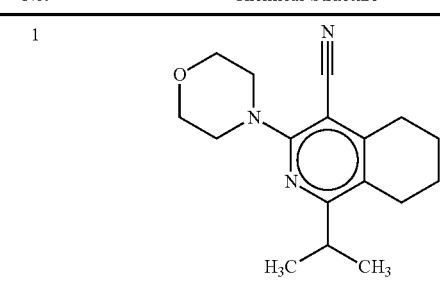 |
| 2 | 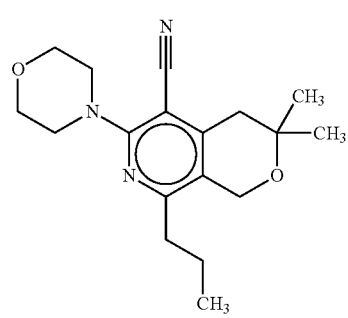 |
| 3 | 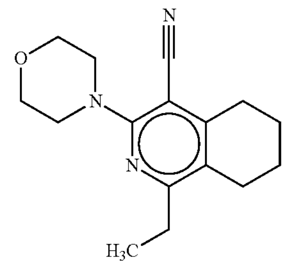 |
| 4 | 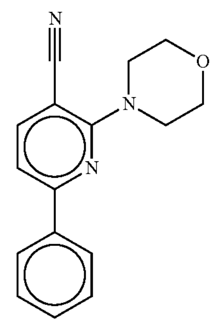 |
| 5 | 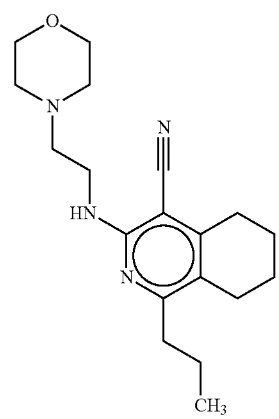 |
| 6 | 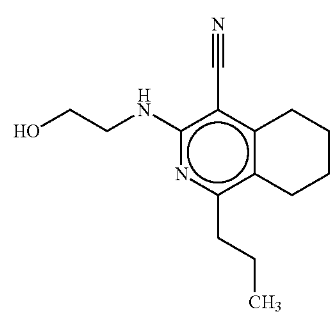 |
| 7 | 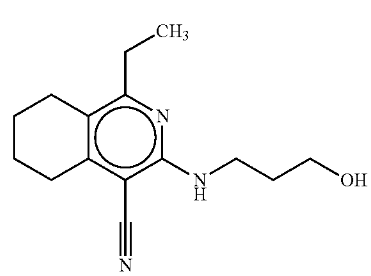 |

-continued

| Compound No. | Chemical Structure |
|---|---|
| 8 | 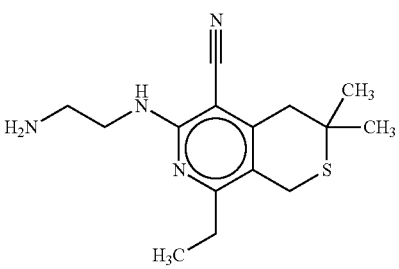 | and the physiologically acceptable salts, solvates, tautomers and stereoisomers thereof, including mixtures thereof in all ratios.

For the avoidance of doubt, if chemical name and chemical structure of the above illustrated compounds do not correspond by mistake, the chemical structure is regarded to unambigously define the compound.

All the above generically or explicitly disclosed compounds, including preferred subsets/embodiments of the herein disclosed formula (I) and Compounds 1 to 8, are hereinafter referred to as compounds of the (present) invention.

The nomenclature as used herein for defining compounds, especially the compounds according to the invention, is in general based on the rules of the IUPAC organisation for chemical compounds and especially organic compounds.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The terms "alkyl" or "A" as well as other groups having the prefix "alk" for the purposes of this invention refer to acyclic saturated or unsaturated hydrocarbon radicals which may be branched or straight-chain and preferably have 1 to 10 carbon atoms, i.e. $C_1$-$C_{10}$-alkanyls, $C_2$-$C_{10}$-alkenyls and $C_2$-$C_{10}$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—CH$_2$CH═CH$_2$; —CH═CH—CH$_3$, —C(═CH$_2$)—CH$_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—CH$_2$—C≡CH, —C≡C—CH$_3$), butynyl, pentynyl, hexynyl, heptynyl, octynyl. Especially preferred is $C_{1-4}$-alkyl. A $C_{1-4}$-alkyl radical is for example a methyl, ethyl, propyl, isopropyl, butyl, isobutyl, tert-butyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Especially preferred are $C_3$-$C_9$-cycloalkyl and $C_4$-$C_8$-cycloalkyl. A $C_4$-$C_8$-cycloalkyl radical is for example a cyclobutyl, cyclopentyl, cyclohexyl, cycloheptyl, cyclooctyl.

The term "heterocyclyl" or "heterocycle" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-aza-bicyclo[2.2.2]octanyl.

The term "aryl" for the purposes of this invention refers to a mono- or polycyclic aromatic hydrocarbon systems having 3 to 14, preferably 5 to 14, more preferably 5 to 10 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula can be effected via any possible ring member of the aryl radical. Examples of suitable "aryl" radicals are phenyl, biphenyl, naphthyl, 1-naphthyl, 2-naphthyl and anthracenyl, but likewise indanyl, indenyl, or 1,2,3,4-tetrahydronaphthyl. The most preferred aryl is phenyl.

The term "heteroaryl" for the purposes of this invention refers to a 3 to 15, preferably 5 to 14, more preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula can be effected via any possible ring member of the heteroaryl radical. Examples of suitable "heteroaryl" are acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl.

For the purposes of the present invention, the terms "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula is via the oxygen atom. Examples are methoxy, ethoxy and n-propyloxy, propoxy, isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula is via the oxygen atom. Examples are cyclopropyloxy, cyclobutyloxy, cyclopentyloxy, cyclohexyloxy, cycloheptyloxy, cyclooctyloxy. Preferred is "$C_3$-$C_9$cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formulae is via the oxygen atom. Examples are pyrrolidinyloxy, thiapyrrolidinyloxy, piperidinyloxy, piperazinyloxy.

The term "aryloxy" for the purposes of this invention refers to an aryl radical according to above definition that is attached to an oxygen atom. The attachment to the compounds of the general formula is via the oxygen atom. Examples are phenyloxy, 2-naphthyloxy, 1-naphthyloxy, biphenyloxy, indanyloxy. Preferred is phenyloxy.

The term "heteroaryloxy" for the purposes of this invention refers to a heteroaryl radical according to above definition that is attached to an oxygen atom. The attachment to the compounds of the general formula is via the oxygen atom. Examples are pyrrolyloxy, thienyloxy, furyloxy, imidazolyloxy, thiazolyloxy.

The term "carbonyl" or "carbonyl moiety" for the purposes of this invention refers to a —C(O)— group.

The term "alkylcarbonyl" for the purposes of this invention refers to a "alkyl-C(O)—" group, wherein alkyl is as defined herein.

The term "alkoxycarbonyl" or "alkyloxycarbonyl" for the purposes of this invention refers to a "alkyl-O—C(O)—" group, wherein alkyl is as defined herein.

The term "alkoxyalkyl" for the purposes of this invention refers to a "alkyl-O-alkyl-" group, wherein alkyl is as defined herein.

The term "haloalkyl" for the purposes of this invention refers to an alkyl group as defined herein comprising at least one carbon atom substituent with at least one halogen as defined herein.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine is most preferred, when the halogens are substituted on an alkyl (haloalkyl) or alkoxy group (e.g. $CF_3$ and $CF_3O$).

The term "hydroxyl" or "hydroxy" means an OH group.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers, such as keto-enol tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:

(i) Wermuth C G et al., Chapter 31: 671-696, The Practice of Medicinal Chemistry, Academic Press 1996;
(ii) Bundgaard H, Design of Prodrugs, Elsevier 1985; and
(iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect— in some circumstances even in more pronounced form.

Any biologically active compound that was converted in vivo by metabolism from any of the compounds of the invention is a metabolite within the scope and spirit of the invention.

There is furthermore intended that a compound of the invention includes isotope-labelled forms thereof. An isotope-labelled form of a compound of the invention is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the inventionby well-known methods include isotopes of hydrogen, carbon, nitrogen, oxygen, phos-phorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the invention, a prodrug, thereof or a pharmaceutically acceptable salt of either which contains one or more of the above-mentioned isotopes and/or other isotopes of other atoms is intended to be part of the present invention. An isotope-labelled compound of the invention can be used in a number of beneficial ways. For example, an isotope-labelled compound of the invention into which, for example, a radioisotope, such as $^{3}H$ or $^{14}C$, has been incorporated is suitable for medicament and/or substrate tissue distribution assays. These radioisotopes, i.e. tritium ($^{3}H$) and carbon-14 ($^{14}C$), are particularly preferred owing to simple preparation and excellent detectability. Incorporation of heavier isotopes, for example deuterium ($^{2}H$), into a compound of the invention has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the invention can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^{2}H$) can also be incorporated into a compound of the invention for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of the invention that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the invention with improved stability through resistance to such oxidative metabolism. Significant improvements in the pharmacokinetic profiles of compounds of the invention are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the invention which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improve-ment in resistance to oxidative metabolism has improved. In this way, it is determined that the half-life of the parent compound can be extended by up to 100% as the result of deuterium-hydrogen exchange of this type.

Deuterium-hydrogen exchange in a compound of the invention can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a ratedetermining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorides, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

By the term "solvate" is meant a hydrate, an alcoholate, or other solvate of crystallization.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

The compounds of the invention are surprisingly characterized by a strong and/or selective modulation, preferably positive allosteric modulation (agonistic activity) of metabotrobic glutamate receptor subtype-3 (mGluR3).

Due to their surprisingly strong and/or selective receptor modulation, the compounds of the invention can be advantageously administered at lower doses compared to other less potent or selective modulators of the prior art while still achieving equivalent or even superior desired biological effects. In addition, such a dose reduction may advantageously lead to less or even no medicinal adverse effects. Further, the high modulation selectivity of the compounds of the invention may translate into a decrease of undesired side effects on its own regardless of the dose applied.

The compounds of the invention being mGluR3 positive allosteric modulators generally have an half maximal effective concentration ($EC_{50}$) of less than about 100 μM, preferably less than about 10 μM, and most preferably less than about 1 μM.

The object of the present invention has surprisingly been solved in another aspect by providing the use of a compound of the invention for modulating metabotropic glutamate receptor subtype 3 (mGluR3) and/or altering glutamate level or glutamatergic signalling.

The terms "modulating, altering, modulation and/or alteration" are intended to refer for the purposes of the present invention to as follows: "partial or complete activating, stimulating, activation and/or stimulation". In this case, it is within the specialist knowledge of the average person skilled in the art to measure and determine such activating, stimulating, activation and/or stimulation by means of the usual methods of measurement and determination. Thus, a partial activating, stimulating, activation and/or stimulation, for example, can be measured and determined in relation to a complete activating, stimulating, activation and/or stimulation.

The object of the present invention has surprisingly been solved in another aspect by providing a process for manufacturing a compound of the invention, comprising the steps of:

(a) reacting a compound of formula (II)

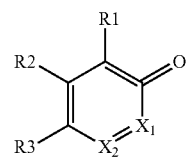

(II)

wherein
R1, R2, R3, X1, X2 are as defined supra,
with a compound of formula (III)

H-V (III)

wherein
V is as defined supra,
to yield the compound of formula (I)

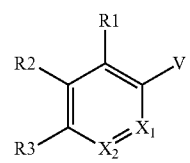

(I)

wherein
V, R1, R2, R3, X1, X2 are as defined supra,
and optionally
(b) converting a base or an acid of the compound of formula (I) into a salt thereof.

Some crude products were subjected to standard chromatography using solvent mixtures containing methanol, ethanol, isopropanol, ethyl acetate, n-hexane, cyclohexane, dichloromethane, n-heptane or petrol ether, respectively.

For a further detailed description of the manufacturing processes, please refer also to the examples and the following general description of the preferred conditions.

A physiologically acceptable salt of a compound of the invention can also be obtained by isolating and/or treating the compound of the invention obtained by the described reaction with an acid or a base.

The compounds of the invention and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the invention. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of a compound of the invention can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used to isolate and/or purify the compounds of the invention.

On the other hand, compounds of the invention can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the compounds of the invention can be liberated from their salts by treatment with strong bases, such as sodium hydroxide, potassium hydroxide, sodium carbonate or potassium carbonate, so long as no further acidic groups are present in the molecule. In the cases where the compounds of the invention have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The object of the present invention has surprisingly been solved in another aspect by providing a medicament comprising at least one compound of the invention.

The object of the present invention has surprisingly been solved in another aspect by providing a medicament comprising at least one compound of the invention for use in the treatment and/or prophylaxis of physiological and/or pathophysiological conditions selected from the group consisting of: "condition which is affected or facilitated by the neuromodulatory effect of mGluR3 allosteric modulators, central nervous system disorders, addiction, tolerance or dependence, affective disorders, such as anxiety, agoraphobia, generalized anxiety disorder (GAD), obsessive-compulsive disorder (OCD), panic disorder, post-traumatic stress disorder (PTSD), social phobia, other phobias, substance-induced anxiety disorder, and acute stress disorder, mood disorders, bipolar disorders (I & II), cyclothymic disorder, depression, dysthymic disorder, major depressive disorder, and substance-induced mood disorder, psychiatric disease, such as psychotic disorders and attention-deficit/hyperactivity disorder, Parkinson's disease, and movement disorders such as bradykinesia, rigidity, dystonia, drug-induced parkinsonism, dyskinesia, tardive dyskinesia, L-DOPA-induced dyskinesia, dopamine agonist-induced dyskinesia, hyperkinetic movement disorders, Gilles de la Tourette syndrome, resting tremor, action tremor, akinesia, akinetic-rigid syndrome, akathisia, athetosis, asterixis, tics, postural instability, postencephalitic parkinsonism, muscle rigidity, chorea and choreaform movements, spasticity, myoclonus, hemiballismus, progressive supranuclear palsy, restless legs syndrome, and periodic limb movement disorder, cognitive disorders such as delirium, substance-induced persisting delirium, dementia, dementia due to HIV disease, dementia due to Huntington's disease, dementia due to Parkinson's disease, Parkinsonian-ALS demential complex, dementia of the Alzheimer's type, substance-induced persisting dementia, and mild cognitive impairment, neurological disorders such as neurodegeneration, neurotoxicity or ischemia such as stroke, spinal cord injury, cerebral hypoxia, intracranial hematoma, memory impairment, Alzheimer's disease, dementia, delirium tremens, other forms of neurodegeneration, neurotoxicity, and ischemia, inflammation and/or neurodegeneration resulting from traumatic brain injury, inflammatory central nervous system disorders, such as multiple sclerosis forms such as benign multiple sclerosis, relapsing-remitting multiple sclerosis, secondary progressive multiple sclerosis, primary progressive multiple sclerosis, and progressive-relapsing multiple sclerosis, migraine, epilepsy and tremor, temporal lobe epilepsy, epilepsy secondary to another disease or injury such as chronic encephalitis, traumatic brain injury, stroke or ischemia, medulloblastomas, inflammatory or neuropathic pain, metabolic disorders associated with glutamate dysfunction, type 2 diabetes, diseases or disorders of the retina, retinal degeneration or macular degeneration, diseases or disorders of the gastrointestinal tract including gastroesophageal reflux disease (GERD), lower esophageal sphincter diseases or disorders, diseases of gastrointestinal motility, colitis, Crohn's disease or irritable bowel syndrome (IBS), cancers." A corresponding use for the preparation of a medicament for the treatment and/or prophylaxis of the aforementioned conditions is intended to be comprised. A corresponding method of treatment administering at least one compound of the invention to a patient in need thereof is also intended to be comprised.

Fur the purpose of medicaments, medical uses and methods of treatments it is preffered that the excluded compounds supra as described and depicted supra are intended to be comprised by the term "compounds of the (present) invention".

Compounds of the invention may be used in combination with one or more other active substances (ingredients, drugs) in the treatment, prevention, suppression or amelioration of diseases or conditions for which compounds of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances (ingredients, drugs) that may be administered in combination with a compound of the invention, and either administered separately or in the same pharmaceutical composition, include, but are not limited to the compounds classes and specific compounds listed in the following:

levodopa, levodopa with selective extracerebral decarboxylase inhibitors, carbidopa, entacapone, COMT inhibitors, dopamine agonists, dopamine receptor agonists, apomorphine, anticholinergics, cholinergic agonists, butyrophenone neuroleptic agents, diphenylbutylpiperidine neuroleptic agents, heterocyclic dibenzazepine neuroleptic agents, indolone neuroleptic agents, phenothiazine neuroleptic agents, thioxanthene neuroleptic agents, NMDA receptor antagonists, MAO-B inhibitors, mGluR3 PAMs or agonists, mGluR4 PAMs or agonists, mGluR5 antagonist or A2A antagonists.

In another aspect of the invention, a medicament according to above aspects and embodiments is provided, wherein in such medicament comprises at least one additional pharmacologically active substance (drug, ingredient).

In a preferred embodiment the at least one pharmacologically active substance is a substance as described herein.

In another aspect of the invention, a medicament according to above aspects and embodiments is provided, wherein the medicament is applied before and/or during and/or after treatment with at least one additional pharmacologically active substance.

In a preferred embodiment the at least one pharmacologically active substance is a substance as described herein.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

In another aspect of the invention, a pharmaceutical composition is disclosed which comprises at least one compound of the invention, at least one pharmacologically active substance other than the compounds of the invention as described herein; and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a kit is provided comprising a therapeutically effective amount of at least one compound of the invention and/or at least one pharmaceutical composition as described herein and a therapeutically effective amount of at least one further pharmacologically active substance other than the compounds of the invention.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the invention and the additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated $NaHCO_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

The contents of all cited references are hereby incorporated by reference in their entirety. The invention is explained in more detail by means of the following examples without, however, being restricted thereto.

EXAMPLES

I. Synthesis of Selected Compounds of the Invention

The following compounds were synthesized and/or characterized. However, it lies in the knowledge of a person skilled in the art to prepare and/or characterize these compounds differently.

Step 1—IS08641-042

1-Isopropyl-3-oxo-2,3,5,6,7,8-hexahydroisoquinoline-4-carbonitrile

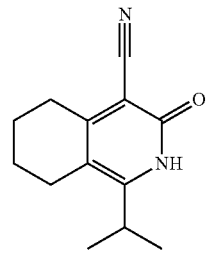 [SMILES: CC(C)c1[nH]c(=O)c(C#N)c2c1CCCC2]

To a solution of 2-isobutyrylcyclohexanone (13 g, 0.0772 mol) in ethanol (250 mL) were added 2-cyano acetamide (6.5 g, 0.0772 mol) and catalytic amount of piperidine (3 mL) at RT. After completion of the reaction (by LCMS), the precipitated solids were collected by filtration and dried under vacuum. It was slurred with ethyl acetate to afford (10 g, 59%) of the titled compound as white solid.

$^1$H NMR (400 MHz, DMSO-$d_6$) δ 11.87 (s, 1H), 3.17-3.10 (m, 1H), 2.74 (s, 2H), 2.50-2.47 (m, 2H), 1.66 (s, 4H), 1.19-1.17 (d, J=7.0 Hz, 6H).

Step 2—FS08641-051

1-Isopropyl-3-morpholin-4-yl-5,6,7,8-tetrahydroisoquinoline-4-carbonitrile (Compound 1)

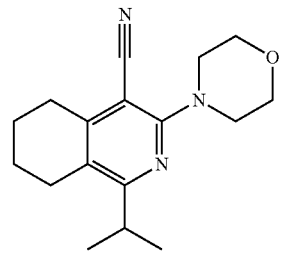 [SMILES: CC(C)c1nc(N2CCOCC2)c(C#N)c2c1CCCC2]

To a solution of 1-Isopropyl-3-oxo-2,3,5,6,7,8-hexahydroisoquinoline-4-carbonitrile (3 g, 0.0138 mol) in DMF (60 mL) were added BOP reagent (4.5 g, 0.0152 mol), diisopropylethylamine (4.8 mL, 0.0277 mol) and morpholine (2.4 mL, 0.0277 mol) at RT. The reaction mixture was stirred at 50° C. for 6 h. After completion of the reaction (by TLC), it was cooled to RT and quenched with water (100 mL). The reaction mixture was extracted with ethyl acetate (2×100 mL). The organic layer was washed with water (100 mL), brine (100 mL), dried over sodium sulphate and evaporated. The crude material was purified by column chromatography using petroleum ether and ethylacetate (9.5:0.5) as an eluent to afford (2.4 g, 60%) of the titled compound as white solid.

TLC: petroleum ether/ethylacetate: (8/2), $R_f$=0.5
LCMS: Mass found (M+1, 286.2)
Method: A—0.1% TFA in $H_2O$, B—0.1% TFA in ACN, Flow—2.0 mL/min.
Column: XBridge C8 (50×4.6) mm, 3.5 μm, +ve mode
Rt (min): 5.8, Area %—97.2
HPLC >98%

Method: A—0.1% TFA in H$_2$O, B—0.1% TFA in ACN, Flow—2.0 mL/min.

Column: XBridge C8 (50×4.6) mm, 3.5 μm,

Rt (min): 5.8, Area %—98.9

$^1$H NMR (400 MHz, DMSO-d$_6$) δ 3.71-3.69 (t, J=9.4 Hz, 4H), 3.48-3.45 (t, J=4.8 Hz, 4H), 3.20-3.12 (m, 1H), 2.78-2.76 (d, J=5.8 Hz, 2H), 2.61-2.59 (d, J=5.6 Hz, 2H), 1.72-1.70 (t, J=3.2 Hz, 4H), 1.13-1.12 (d, J=6.6 Hz, 6H).

The following compounds of the invention are commercially available:

| Compound No. | Cat. No. | Commercial Source |
|---|---|---|
| 4 | Amb17360718 | Ambinter |
| 3 | 5921-0170 | ChemDiv |
| 8 | STOCK1S-60655 | Interbioscreen |
| 7 | 5921-0172 | ChemDiv |
| 2 | 8640-0536 | ChemDiv |
| 6 | STOCK1S-39100 | Interbioscreen |
| 5 | STOCK6S-08899 | Interbioscreen |

TABLE 1

| Compound No. | LC/MS RT (min) | LC/MS m/z [M + H] | HEK293T-mGluR3-Gqi5 Calcium Mobilization Assay (EC$_{50}$) A > 10 μM B = 1-10 μM C < 1 μM |
|---|---|---|---|
| 1 | | | C |
| 2 | | | B |
| 3 | | | B |
| 4 | | | B |
| 5 | | | B |
| 6 | | | B |
| 7 | | | B |
| 8 | | | B |

II. Biological Assays

HEK293T-mGluR3-Gqi5 Calcium Mobilization Assay

Reagents:

Cells: HEK293T-mGluR3-Gqi5 Stable Cell Line (MultiSpan cat# CG1190)

Culture Medium:

DMEM-GlutaMAX-1 (GIBCO #10566)+10% FBS (dialyzed & heat-inactivated, Hyclone cat# SH 30079.03), 2 mM sodium pyruvate (GIBCO #11360), 1 μg/ml puromycin (GIBCO #0399) and 250 ug/ml hygromycin (GIBCO #10687-010) HBSS (GIBCO #14025), add HEPES at 20 mM for a pH of 7.4

384 well cell plate: poly-D-lysine-coated, black/clear bottom microplates (Corning cat#3845)

Ca$^{2+}$ dye: FLIPR Ca-4 assay kit (Molecular Devices cat# R8142)

L-Glutamate (Sigma cat #2834)

Cell Plating

Plate 8000 cells per well (1×10$^5$ cells/ml, in 80 μl) in a black, clear bottom, 384 well plate (Corning 3845). Incubate the cell plate for 30 minutes at RT and then incubate the cells 37° C., 5% CO$_2$ for 16-24 hours before the assay.

Ca$^{2+}$ Assay Using the FLIPR

Wash the cells with HBSS 3 times using the Bravo automated pipettor. The remaining volume of HBSS is 20 μl per well.

Add 20 μl of dye loading solution to each well and incubate the cells at 37° C., 5% CO$_2$ for 1 hour.

Prepare Compound Plate:

Serial dilute test compounds in DMSO at a 1:4 ratio, starting at al 0 mM concentration. Transfer 500 nl of the diluted compounds to a Matrix plate and add 30 μl of 37° C. HBSS, by Multidrop, to each well. The final starting concentration of the compounds is 33 uM.

Prepare a solution of L-Glutamate in HBSS at 5× the EC20 concentration. Transfer to a 384 well Matrix plate using a Multidrop. The EC20 concentration is determined by a test plate before the screen.

Assay:

Ca$^{2+}$ fluorescence is measured in the cells using the FLIPR Tetra (Molecular Devices). Following a baseline recording of the wells for 1 minute, add 10 ul of the diluted (5×) compounds to the cell plate and record for 3 minutes. Add 12.5 ul of 5×L-glutamate to the cells and record for an additional 5 minutes.

Instrument settings: excitation at 485 nm, emission at 525 nm.

The measured half maximal effective concentration (EC$_{50}$) of the compounds of the invention is displayed in table 1.

The invention claimed is:

1. A method for modulating metabatropic glutamate receptor subtype 3, said method comprising administering to a patient in need thereof a compound selected from the group consisting of:

| Compound No. | Chemical Structure |
|---|---|
| 1 | 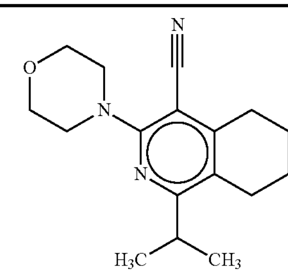 |
| 3 | 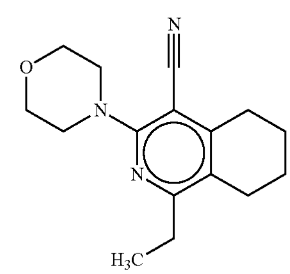 |
| 6 | 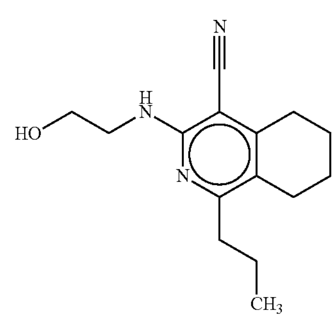 |

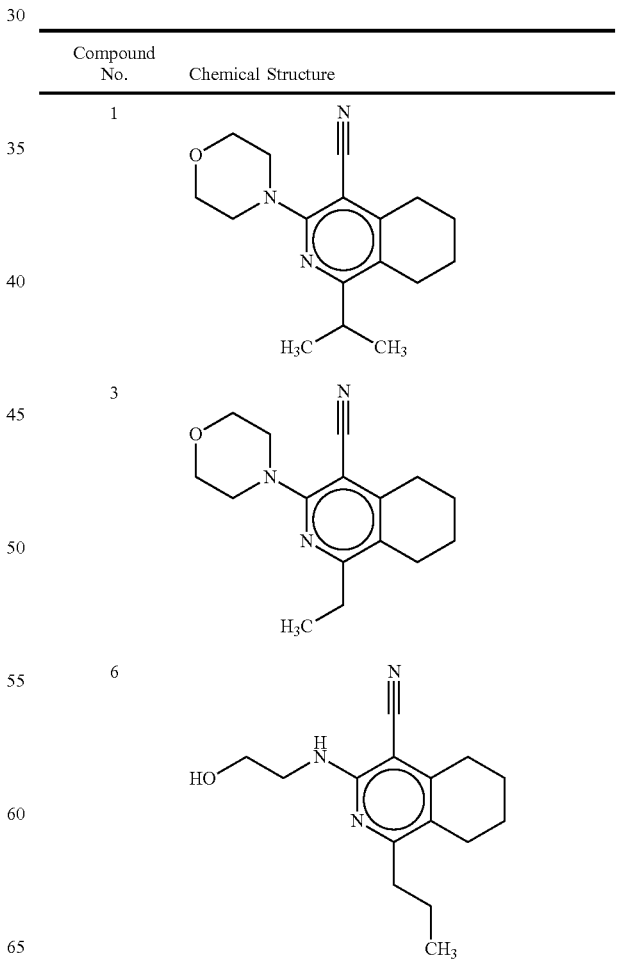

| Compound No. | Chemical Structure |
|---|---|
| 7 | (structure: tetrahydroisoquinoline with CH₃, CN, and NH-CH₂CH₂CH₂-OH substituents) |
| 8 | (structure: pyridine fused with thiopyran bearing gem-dimethyl, with CN, NH-CH₂CH₂-NH₂, and CH₂CH₃ substituents) | and physiologically acceptable salts, solvates, tautomers and stereoisomers thereof, including mixtures thereof in all ratios.

2. The method according to claim 1, wherein said patient is human.

3. The method according to claim 1, wherein said compound is administered to said patient in an amount between 0.5 mg and 100 mg per dose unit.

4. The method according to claim 1, wherein said compound is administered to said patient in an amount between 0.001 mg/kg and 10 mg/kg of body weight.

5. A method for treating Parkinson's disease, said method comprising administering to a patient in need thereof a compound selected from the group consisting of:

| Compound No. | Chemical Structure |
|---|---|
| 1 | (structure: tetrahydroisoquinoline with morpholino, CN, and CH(CH₃)₂ substituents) |
| 3 | (structure: tetrahydroisoquinoline with morpholino, CN, and CH₂CH₃ substituents) |
| 6 | (structure: tetrahydroisoquinoline with CN, NH-CH₂CH₂-OH, and CH₂CH₂CH₃ substituents) |
| 7 | (structure: tetrahydroisoquinoline with CH₂CH₃, CN, and NH-CH₂CH₂CH₂-OH substituents) |
| 8 | (structure: pyridine fused with thiopyran bearing gem-dimethyl, with CN, NH-CH₂CH₂-NH₂, and CH₂CH₃ substituents) |

6. The method according to claim 5, wherein said patient is human.

7. The method according to claim 5, wherein said compound is administered to said patient in an amount between 0.5 mg and 100 mg per dose unit.

8. The method according to claim 5, wherein said compound is administered to said patient in an amount between 0.001 mg/kg and 10 mg/kg of body weight.

* * * * *